US00PP30659P3

(12) United States Plant Patent
Nicolaï

(10) Patent No.: US PP30,659 P3
(45) Date of Patent: Jul. 9, 2019

(54) APPLE TREE NAMED 'ZOUK 16'

(50) Latin Name: *Malus domestica*
Varietal Denomination: ZOUK 16

(71) Applicant: Zouk B.V.B.A., Sint-Truiden (BE)

(72) Inventor: Johan Nicolaï, Sint-Truiden (BE)

(73) Assignee: Zouk B.V.B.A., Sint-Truiden (BE)

( * ) Notice: Subject to any disclaimer, the term of this patent is extended or adjusted under 35 U.S.C. 154(b) by 0 days.

(21) Appl. No.: 15/732,496

(22) Filed: Nov. 20, 2017

(65) Prior Publication Data

US 2019/0159375 P1 May 23, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

(56) References Cited

U.S. PATENT DOCUMENTS

PP4,121 P 10/1977 ten Hove
PP6,450 P 12/1988 Visser
PP6,955 P 8/1989 Kiddle
PP16,559 P3 5/2006 Nicolai
PP17,201 P3 11/2006 Nicolai
PP25,671 P3 7/2015 Kellerhals
2004/0025211 P1 2/2004 Zulch

OTHER PUBLICATIONS

U.S. Appl. No. 15/732,499, "Apple Tree Named 'ZOUK 31'," filed Nov. 20, 2017, for inventor Johan Nicolai and for applicant Zouk B.V.B.A.
U.S. Appl. No. 15/732,497, "Apple Tree Named 'ZOUK 32'," filed Nov. 20, 2017, for inventor Johan Nicolai and for applicant Zouk B.V.B.A.
U.S. Appl. No. 15/732,502, "Apple Tree Named 'ZOUK G1'," filed Nov. 20, 2017, for inventor Johan Nicolai and for applicant Zouk B.V.B.A.
Fresh Plaza (2016). "Johan Nicolai presents new early Gala variety," retrieved on Oct. 16, 2018, retrieved from the Internet at http://www.freshplaza.com/article/2153468/johan-nicolai-presents-new-early-gala-variety/, 2 pp.
Guerra (2017). "Strains improve standard varieties translated and edited by Julia Strobl," European Fruit Network Jun. 2017, retrieved on Oct. 22, 2018, retrieved from the Internet at http://kp.eufrin.eu/fileadmin/user_upload/documents/804-14df1cca1323ccb72d8b027c37356dfd.pdf, pp. 14-17.
Horticulture Week (2015). "Apple varieties found by chance unveiled at show," retrieved on Oct. 22, 2018, retrieved from the Internet at https://www.hortweek.com/apple-varieties-found-chance-unveiled-show/fresh-produce/article/1370357, 2 pp.

*Primary Examiner* — Keith O. Robinson
(74) *Attorney, Agent, or Firm* — Morrison & Foerster LLP

(57) ABSTRACT

A new and distinctive variety of a *Malus domestica* apple tree, named 'ZOUK 16' that is distinguished by its well-feathered tree with a bright green leaf-color and its pink-skinned bicolor fruit that is characterized as a dessert apple of premium quality and bright white flesh, is disclosed.

5 Drawing Sheets

Latin name:
Botanical classification: *Malus domestica.*
Varietal denomination: The varietal denomination of the claimed apple tree variety is 'ZOUK 16'.

BACKGROUND OF THE INVENTION

Apples are an economically important crop. Accordingly, there exists a need to develop new varieties of apple tree with improved characteristics, such as fruit appearance and taste.

BRIEF SUMMARY OF THE INVENTION

In order to meet these needs, the present invention is directed to an improved variety of apple tree. In particular, the invention relates to a new and distinct variety of apple tree (*Malus domestica*), which has been denominated as 'ZOUK 16'.

Apple tree variety 'ZOUK 16' is a hybrid that was discovered in Sint-Truiden, Belgium as a hybrid from a controlled pollination cross of seed parent 'Nicogreen' (U.S. Plant Pat. No. 16,559) and pollen parent 'Nicoter' (U.S. Plant Pat. No. 17,201). The original seedling of the new variety was first asexually propagated by T-budding and bench grafting onto 'M9 T337' (also known as 'M9 NAKBT337' or 'M9'; unpatented) rootstock, 'MM106' (also known as 'Malling-Merton 106'; unpatented) rootstock, and 'MM111' (also known as 'Malling-Merton 111'; unpatented) rootstock in 2013 and subsequently planted in a nursery bed for tree production.

The original 'ZOUK 16' tree and its progeny have been observed growing in a plot located in Gorsem, Belgium. The new variety produces fruit that matures for commercial harvesting approximately at the end of September in the Haspengouw area in Belgium.

The 'ZOUK 16' apple tree variety is distinguished from other apple tree varieties by the following unique combination of characteristics: the new variety is a well-feathered tree with a bright green leaf-color that produces pink-skinned bicolor fruit that is characterized as a dessert apple of premium quality by its taste, texture, and bright white flesh.

Asexual reproduction of the 'ZOUK 16' apple tree variety by T-budding and bench grafting onto 'M9 T337', 'MM106' and 'MM111' rootstocks in Sint-Truiden, Belgium shows that the foregoing and all other characteristics and distinctions are true to type and are established and transmitted through succeeding asexual propagations.

BRIEF DESCRIPTION OF THE DRAWINGS

The 'ZOUK 16' apple tree variety is illustrated by the accompanying photographs which show fruit of the tree, as well as flowers. The colors shown are as true as can be reasonably obtained by conventional photographic procedures. However, the colors in the photographs may vary with lighting conditions and, therefore, color characteristics of this new variety should be determined with reference to the observations described herein, rather than from the photographs alone. The photographs are from trees that are four years old.

DETAILED BOTANICAL DESCRIPTION

Figure 1:
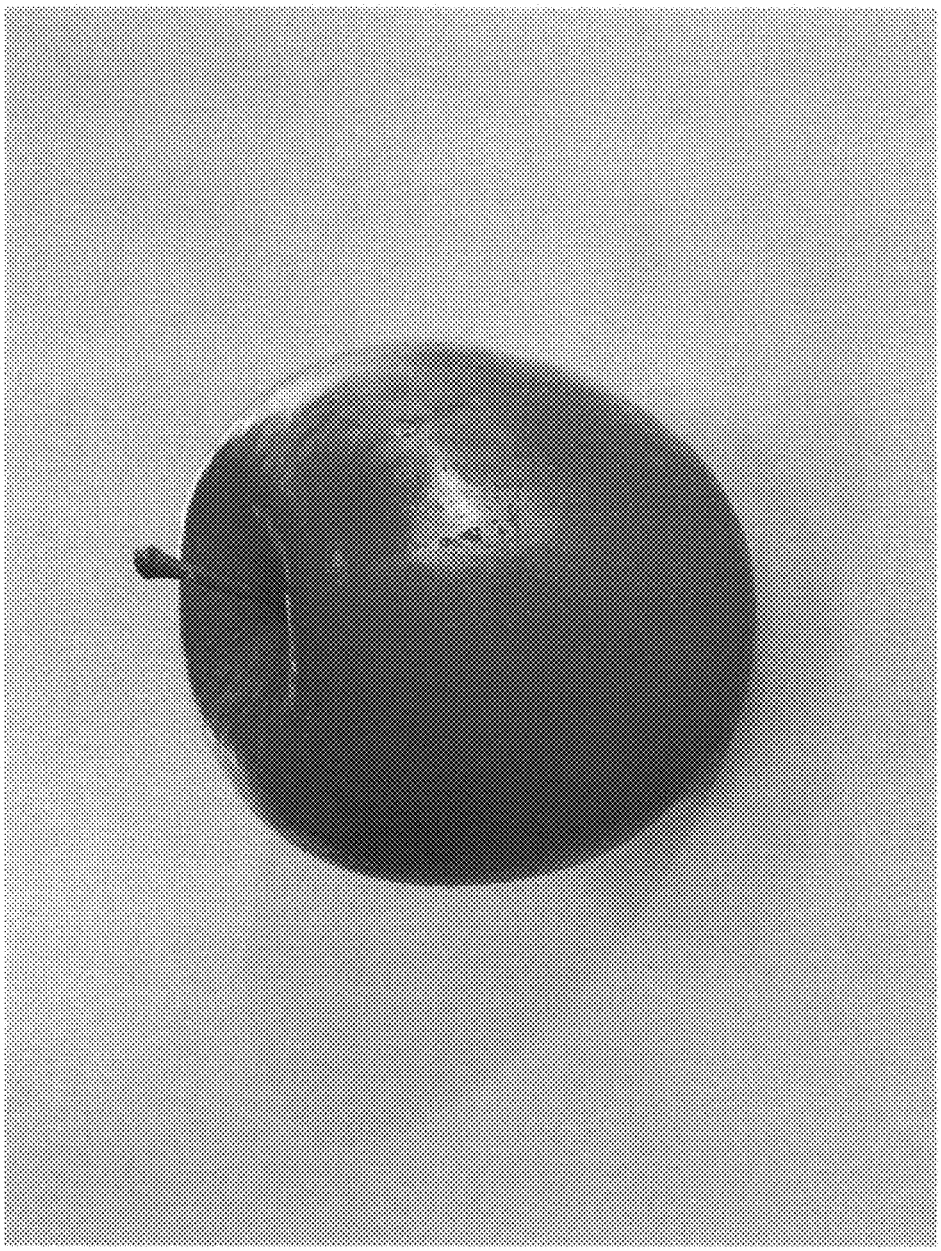
FIG. 1 illustrates a fruit of apple tree variety 'ZOUK 16'.
Figure 2:
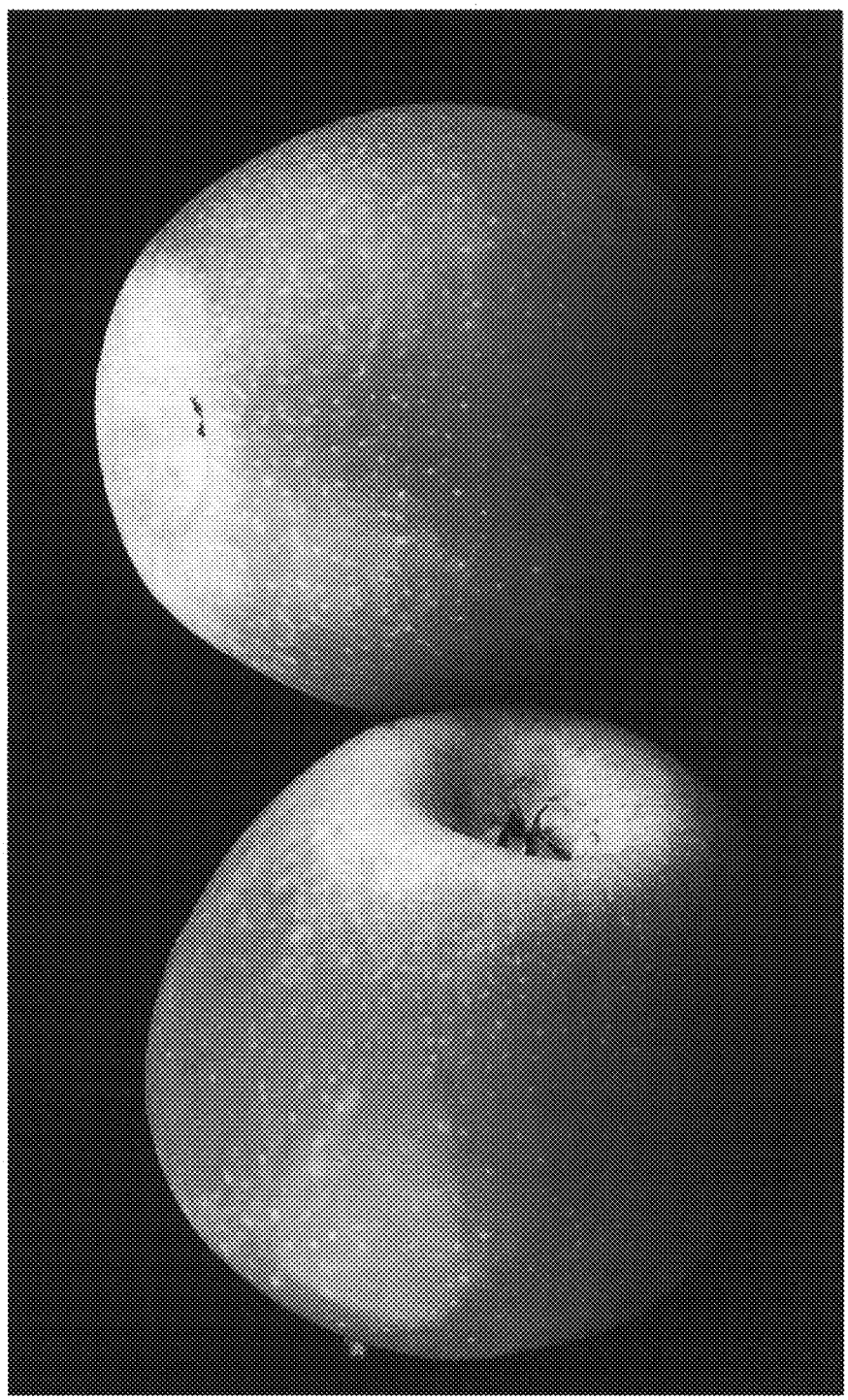
FIG. 2 illustrates the colored side of fruit with the typical concave-shaped basin of apple variety 'ZOUK 16'.
Figure 3:
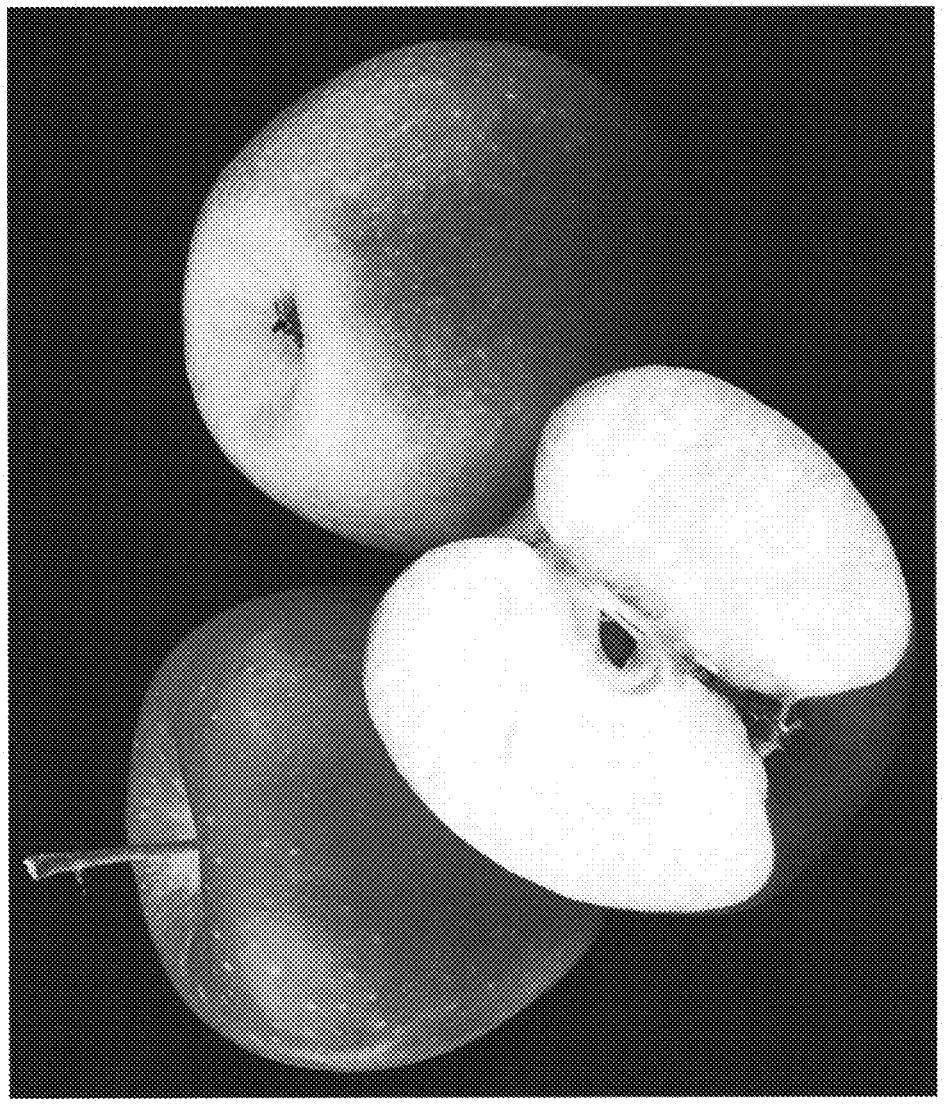
FIG. 3 illustrates fruit of apple tree variety 'ZOUK 16' cut in half to view the inside flesh of the fruit.
Figure 4:
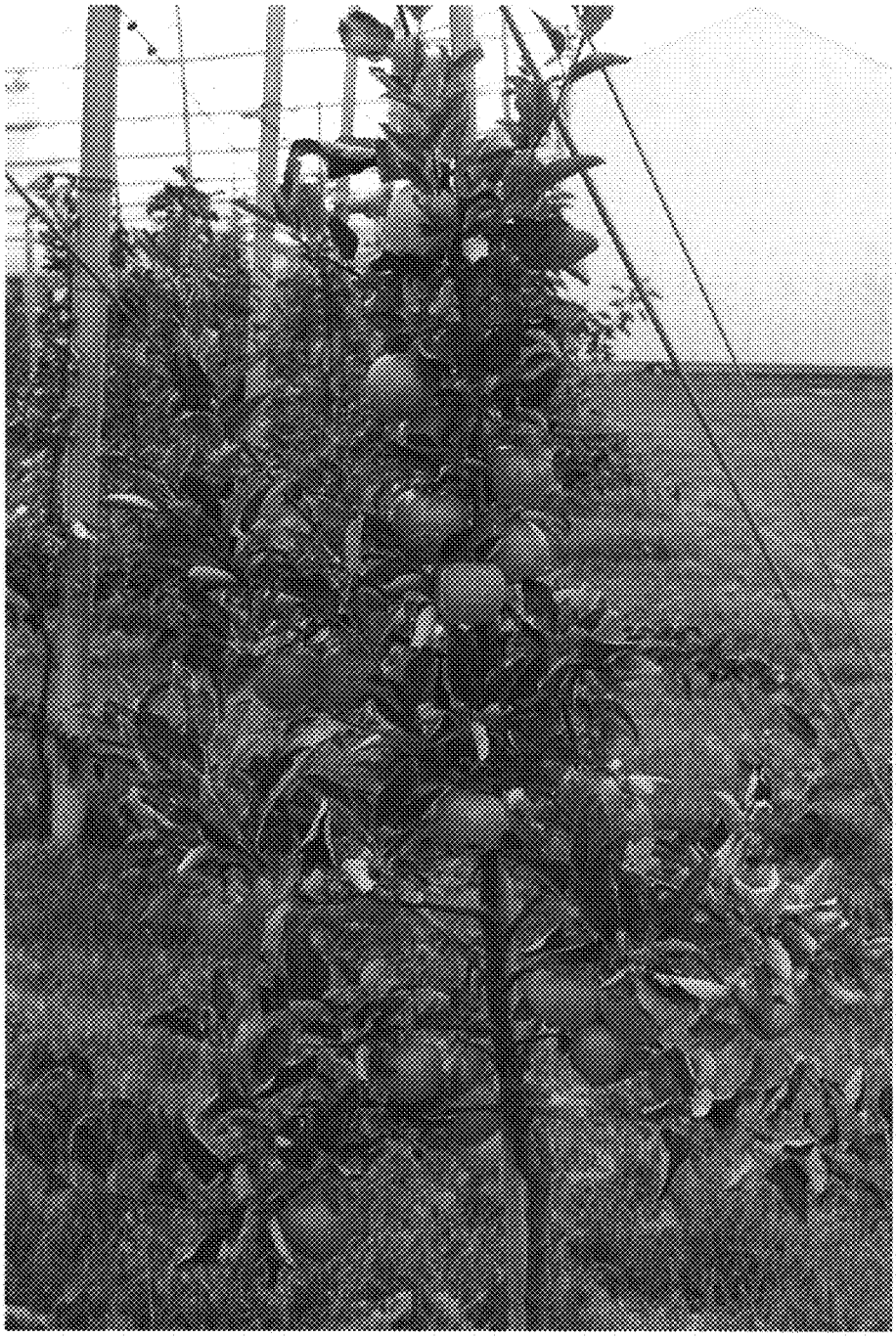
FIG. 4 illustrates a tree of apple tree variety 'ZOUK 16' with fruit on the tree (colored side).
Figure 5:
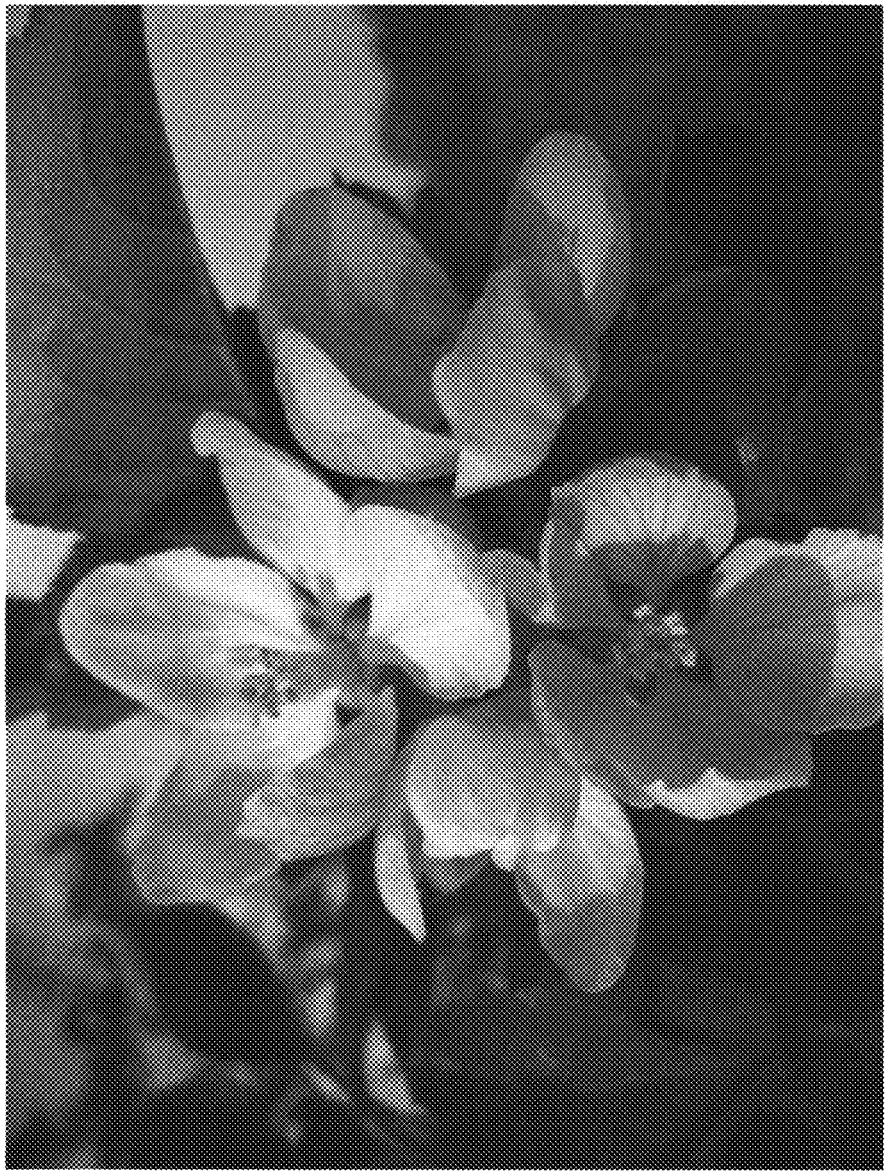
FIG. 5 illustrates flowers of apple tree variety 'ZOUK 16'.

The following description sets forth the distinctive characteristics of 'ZOUK 16'. The following botanical description of 'ZOUK 16' is based on observations of the originally identified tree, and asexually reproduced progeny, grown on 'M9 T337' rootstock in Sint-Truiden, Belgium. Referring more specifically to the details of the new and distinct variety of apple tree, unless otherwise stated, the following has been observed on trees that were four years of age growing on 'M9 T337' rootstock in Sint-Truiden, Belgium. Numbers provided are averages of data measured from the sampling trees.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. All color references are from The R.H.S. Colour Chart of The Royal Horticultural Society of London (R.H.S.) (Sixth Edition, 2015).

Tree:

*Vigor.*—Moderate (comparable to 'Golden Delicious' (unpatented)).

*Overall shape.*—Spreading.

*Height.*—Approximately 3.0 m.

*Width.*—Approximately 1.45 m.

*Caliper.*—Approximately 40 mm at 50 mm above the graft union.

*Trunk bark texture.*—Smooth with raised, prominent lenticels of 1 mm.

*Trunk bark color.*—Light olive grey (RHS 197B).

*Patches or other markings.*—No prominent spots or scales evident.

*Primary branches.*—Stout; branches emerge at an angle of approximately 60 to approximately 90 degrees with branches higher in the tree emerging at approximately 60 degrees. Measured trees are grown to a central leader system. The typical and observed lateral branch length is 80 cm (first primary branch as a one-year old shoot).

*Branch color.*—One-year-old branches are moderate yellowish brown (RHS N199C) in color, while older branches are moderate olive brown (RHS N199A) in color.

*Branch pubescence.*—Very slight pubescence on one-year-old branches.

*Branch lenticels.*—Medium density, approximately 6 per square centimeter. Shape: Oval. Color: Yellowish grey (RHS 156C). Size: Approximately 1 mm long.

*Internodes.*—Average internode length is 34.8 mm for a one-year-old shoot.

*Lenticel density on shoot.*—6 lenticels per square centimeter for a one-year old shoot.

*Lenticel shape on shoot.*—Mostly oval with a few of the smaller ones having a round shape for a one-year-old shoot.

*Bearing.*—Annual.

*Hardiness.*—European Zone 8 hardy (comparable to 'Royal Gala' (U.S. Plant Pat. No. 4,121) and 'Golden Delicious' (unpatented)).

*Disease resistance.*—Sensitive to apple scab caused by *Venturia inaequalis.*

Leaves:

*Texture.*—Upper leaf surface: Slightly hairy. Lower leaf surface: Hairy.

*Sheen.*—Upper leaf surface: Medium glossy. Lower leaf surface: Not glossy.

*Length.*—Average approximately 121 mm.

*Width.*—Average approximately 68 mm.

*Margin.*—Serrate.

*Tip shape.*—Acute.

*Stipules.*—2 present on each leaf. Width: 3 mm. Length: 15 mm.

*Leaf color.*—Upper leaf surface: Vivid yellowish green (RHS 134A). Lower leaf surface: Light yellowish green (RHS 134D).

*Leaf vein color.*—Pale yellowish green (RHS 157C).

*Leaf blade attitude in relation to the shoot.*—Upwards.

*Petiole length.*—Average approximately 43 mm.

Flower:

General:

*Size.*—Medium. Diameter: Between 48 and 56 mm, with an average of 52 mm.

*Shape.*—Ovoid to round.

*Flower bud color.*—Closed flower buds: RHS 186B. Open flower buds: White (RHS NN155D) with purple tips (RHS 186C).

Petals:

*Numbers of petals per flower.*—5.

*Length.*—25 mm.

*Width.*—15 mm.

*Shape.*—Ovate. Base: Acuminate. Apex: Rounded.

*Arrangement.*—Separated but overlapping.

*Color.*—Upper petal surface: White (RHS NN155D) with pink-purple veins (RHS 186C). Lower petal surface: White (RHS NN155C) to vivid purplish pink (RHS N66B).

Sepals:

*Number.*—About 5 per flower.

*Length.*—10 to 12 mm.

*Width.*—3 to 4 mm.

*Color.*—Deep yellowish green (RHS 141A).

*Arrangement.*—Arranged separately.

Pedicel/peduncle: Apples do not have branched inflorescences and hence do not have pedicels. The flower stalk of an apple is the peduncle.

*Length.*—25 to 30 mm.

*Diameter.*—1 to 2 mm.

*Color.*—Moderate yellow-green (RHS 138C).

Stamen:

*Number.*—Approximately 20 per flower, arranged in a row around the circumference of the receptacle.

*Length.*—10 mm.

*Filament color.*—Pale yellow green (RHS 155A).

*Anthers.*—About 20 per flower. Color: Pale yellow (RHS 8D).

*Pollen color.*—Vivid yellow (RHS 17B).

*Amount of pollen.*—Abundant.

Pistil:

*Stigma length.*—7 mm.

*Styles.*—Fused.

*Color.*—Green yellow (RHS 1B).

Pollination requirements: Later flowering varieties, e.g., 'Granny Smith' (unpatented) or 'Idared' (unpatented), will overlap sufficiently in flowering to enable pollination.

Fragrance: Slight, apple-blossom-like.

Bloom season (time of beginning of flowering): In 2017 in Velm, Belgium, blooming began on the 20$^{th}$ of April with full bloom on the 28$^{th}$ of April, finishing on the 9$^{th}$ of May (in comparison, seed parent 'Nicoter' was in full bloom on the 18$^{th}$ of April).

Fruit:

General: Measurements are the average of 10 typical 'ZOUK 16' apples.

*Eye.*—Erect divergent. Size: 1.2 mm.

Size: Medium to large.

*Length.*—Approximately 75 mm.

*Width.*—Approximately 82.5 mm.

Shape: Globose to globose-conical. The calyx is 73% closed and 27% open, with an average opening size of 5 mm.

*Cavity.*—Shape: Acute. Depth: 14.3 mm. Width: 30.4 mm.

*Basin.*—Shape: Concave. Width: 29.4 mm. Depth: 9.8 mm.

Fruit stem:

*Length.*—Average 30 mm.

*Diameter.*—Average 3 mm.

*Color.*—Strong yellowish brown (RHS N199D).

Locules: 5 slightly open locules with seeds free of the carpel wall at maturity.

Fruit skin:

*Tendency to crack.*—Absent.

*Thickness.*—Thin.

*Surface texture.*—Glossy and smooth.

*Lenticels.*—Present. Diameter: Approximately 0.5 to 1.0 mm. Color: Yellowish white (RHS 155D).

*Color.*—General color effect: Bright pink to red (RHS 53D). Ground color: At maturity, about yellow-green (RHS 154C). Over color: Bright pink to red (RHS 58D), very occasionally with pale, light yellowish pink stripes (RHS 29C).

*Russetting.*—Almost none, from time to time a very minimal amount inside the stem cavity.

*Bloom.*—Moderate.

Fruit flesh:

*Flavor.*—Fresh and mild, a good balance between sweet and sour.

*Brix.*—Average approximately 14 Brix.

*Juiciness.*—Very juicy.

*Color.*—White (RHS 155A).

*Aroma.*—Apple-like and moderate in intensity.

*Firmness.*—Firm.

Core: The calyx is open in about 5 percent of fruit, the calyx tube is open and the core lines are defined.

*Shape.*—Slightly elongate.

*Diameter.*—25 mm.

*Number of bundles.*—Approximately 10 per fruit.

*Length.*—32 mm.

*Calyx tube length.*—5 mm.

Seed:

*Number.*—About 1 to 2 seeds per cell.

*Shape.*—Acute.

*Length.*—8 to 9 mm.

*Width.*—5 mm.

*Color.*—Moderate reddish brown (RHS 175A).

Fruit production (time of fruit eating maturity): The first picking date (early for long storage) in the 2017 season in Belgium was the 15$^{th}$ of September, the main picking date was about the 25$^{th}$ of September, and the last picking date was the 30$^{th}$ of September.

Storage: Fruit is not sensitive to low temperature decay and stores well at about 1° C. or about 34° F. Fruit can be stored for at least six months. Fruit reacts very well to 1-MCP treatment, which also improves the shelf life.

Usage: Fresh eating.

COMPARISONS TO PARENTAL AND SIMILAR VARIETIES

The 'ZOUK 16' apple tree variety is distinguished from its seed parent, 'Nicogreen', by the following unique combination of characteristics: fruit of 'ZOUK 16' matures approximately one week earlier than fruit of 'Nicogreen'; and fruit of 'ZOUK 16' has a bright pink color, whereas fruit of 'Nicogreen' has a yellow-green color.

The 'ZOUK 16' apple tree variety is distinguished from pollen parent 'Nicoter' by the following unique combination of characteristics: fruit of 'ZOUK 16' matures approximately one week later (fourth week of September) than fruit of 'Nicoter' (third week of September); 'ZOUK 16' produces more fruit than does 'Nicoter'; and fruit of 'ZOUK 16' has a pink color, whereas fruit of 'Nicoter' has a bright red to dark red color on a green-yellow background.

The 'ZOUK 16' apple variety is distinguished from similar apple tree variety 'Cripps Pink' (U.S. Plant Pat. No. 7,880) by producing fruit that matures more than one month earlier than the fruit of 'Cripps Pink'. In addition, the fruit of 'ZOUK 16' is much juicier than the fruit of 'Cripps Pink' and differs in flavor from the fruit of 'Cripps Pink'. Further, the flesh of 'ZOUK 16' fruit oxidizes and turns brown more slowly than the flesh of 'Cripps Pink' fruit. Moreover, the shape of the fruit of 'ZOUK 16' (globose to globose-conical) is somewhat higher than the shape of the fruit of 'Cripps Pink' (asymmetrical, ellipsoid prominent ribbed surface; medium distal crowns, rounded at base, sides slightly unbroken, unequal). Therefore, despite the over color of fruit of 'ZOUK 16' being similar to the over color of fruit of 'Cripps Pink', 'ZOUK 16' fruit is clearly distinguished from 'Cripps Pink' fruit. In addition, the spreading tree shape of 'ZOUK 16' is different and distinguishable from the upright tree shape of 'Cripps Pink'.

What is claimed is:

1. A new and distinct variety of apple tree named 'ZOUK 16' as shown and described herein.

* * * * *